United States Patent
Ovchinnikov et al.

(10) Patent No.: US 11,185,623 B2
(45) Date of Patent: Nov. 30, 2021

(54) ON-DEMAND FLUIDICS SYSTEM CONTROL BASED ON FREQUENCY-DOMAIN PROCESSING

(71) Applicant: Alcon Inc., Fribourg (CH)

(72) Inventors: Mikhail Ovchinnikov, Dana Point, CA (US); Satish Yalamanchili, Irvine, CA (US)

(73) Assignee: Alcon Inc., Fribourg (CH)

(*) Notice: Subject to any disclaimer, the term of this patent is extended or adjusted under 35 U.S.C. 154(b) by 595 days.

(21) Appl. No.: 15/870,416

(22) Filed: Jan. 12, 2018

(65) Prior Publication Data
US 2018/0207330 A1    Jul. 26, 2018

Related U.S. Application Data

(60) Provisional application No. 62/449,795, filed on Jan. 24, 2017.

(51) Int. Cl.
*A61M 1/00* (2006.01)
*A61F 9/007* (2006.01)
*A61B 90/00* (2016.01)

(52) U.S. Cl.
CPC ......... *A61M 1/743* (2021.05); *A61F 9/00736* (2013.01); *A61F 9/00745* (2013.01); *A61M 1/0058* (2013.01); *A61M 1/73* (2021.05); *A61M 1/774* (2021.05); *A61M 1/85* (2021.05); *A61B 2090/064* (2016.02); *A61B 2217/005* (2013.01); *A61B 2217/007* (2013.01); *A61M 2205/3334* (2013.01); *A61M 2205/3337* (2013.01); *A61M 2205/3344* (2013.01); *A61M 2205/50* (2013.01); *A61M 2210/0612* (2013.01)

(58) Field of Classification Search
CPC .............. A61M 1/0035; A61M 1/0025; A61M 1/0058; A61M 1/0064; A61M 1/0084; A61F 9/00736; A61F 9/00745
USPC .......................................... 604/22
See application file for complete search history.

(56) References Cited

U.S. PATENT DOCUMENTS

| 2015/0157501 | A1* | 6/2015 | Bourne | ............... A61M 1/0058 |
| | | | | 604/22 |
| 2015/0290372 | A1* | 10/2015 | Muller | ............... A61M 60/857 |
| | | | | 600/424 |

* cited by examiner

*Primary Examiner* — Phillip A Gray

(57) ABSTRACT

Frequency-domain signal processing of pressure sensor signals and/or flow signals is used to provide on-demand control of a multi-component fluidic system. An example method, implemented in a phacoemulsification system comprises receiving a signal from each of one or more sensors, the one or more sensors comprising at least one pressure sensor, and converting each of one or more of the received signals, including at least one signal from a pressure sensor, to a frequency-domain representation of the received signal. The method further comprises identifying, based on the frequency-domain representations of received signals, at least one event from a set of predetermined events, and controlling one or more fluid control devices, responsive to the identifying.

15 Claims, 5 Drawing Sheets

ON-DEMAND FLUIDICS SYSTEM CONTROL BASED ON FREQUENCY-DOMAIN PROCESSING

TECHNICAL FIELD

The present disclosure generally relates to control systems for regulating the flow of fluids, and more particularly relates to techniques for regulating fluid flow in phacoemulsification surgical equipment.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During a phacoemulsification procedure, a tip of a needle is inserted into the anterior segment of the eye through a small incision in the outer tissue of the eye. The surgeon brings the tip of the needle into contact with the lens of the eye, so that the vibrating tip fragments the lens. The resulting fragments are aspirated out of the eye through an interior bore of the needle, along with irrigation solution provided to the eye during the procedure.

A common complication during the phacoemulsification process arises from a blockage, or occlusion, of the lumen of the needle while aspirating material from the eye. As the irrigation fluid and emulsified tissue is aspirated away from the interior of the eye through the hollow needle, pieces of tissue that are larger than the diameter of the needle's bore may become lodged within the bore. While the needle is occluded, vacuum pressure builds up within the needle. An occlusion break is when the occlusion is removed, which results in a sudden surge of flow through the needle. This sudden flow results in a sudden reduction of pressure within the needle and the eye. The resulting drop in pressure in the anterior chamber of the eye when the occlusion is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

Other non-ideal scenarios that may occur during surgery include a so-called water-hammer effect, where an undesirable pressure wave propagates through the fluid system as the result of a valve closure. Thermal changes can also present challenges for the fluid control systems in phacoemulsification equipment, which generally seek to reduce post-occlusion surge while maintaining a stable intraocular pressure (IOP) throughout varying flow conditions. Accordingly, there remains a need for improved fluidics system control in phacoemulsification systems

SUMMARY

Providing stable control of fluid flow in phacoemulsification equipment is complicated by events such as post-occlusion surge and water hammer, as well as by thermal changes within and across the system. The effects of these non-ideal events and the system fluid pressure can be on the same order of magnitude as changes in pressure caused by the equipment user's interaction with the equipment, or on the same order of magnitude as noise in the feedback signals. In systems where the fluid flow is controlled based on feedback from one or more pressure sensors, as described below, this can make it difficult for the control system to discern the difference between those signals for which immediate compensation by the control system is desirable, and those signals for which rapid compensation is less desirable.

The techniques and apparatus disclosed herein address these difficulties by applying signal processing of pressure sensor signals and/or flow signals in the frequency domain, to provide on-demand control of multi-component fluidic systems. Using these techniques, changes in the frequency and/or phase of the pressure or flow signals can be detected, allowing the detection of and compensation for events that may be undetectable from the raw, time-domain, sensor signals. As illustrated in the detailed description that follows, these techniques may be especially useful in systems with fast time constants, and when the magnitude of noise in the signals is comparable to the magnitude of signal changes due to actual events.

An example method, according to some embodiments of the presently disclosed techniques, comprises: receiving a signal from each of one or more sensors, the one or more sensors comprising at least one pressure sensor, and converting each of one or more of the received signals, including at least one signal from a pressure sensor, to a frequency-domain representation of the received signal. The method further comprises identifying, based on the frequency-domain representations of received signals, at least one event from a set of predetermined events, and controlling one or more fluid control devices, responsive to the identifying.

Also disclosed herein are control systems for a phacoemulsification system. An example control system corresponds to the above-summarized method and comprises: one or more sensors, the one or more sensors comprising at least one pressure sensor; one or more fluid control devices; and controller circuitry operatively coupled to the one or more sensors and the one or more fluid control devices. The controller circuitry is configured to convert each of one or more of the received signals, including at least one signal from a pressure sensor, to a frequency-domain representation of the received signal, and to identify, based on the frequency-domain representations of received signals, at least one event from a set of predetermined events. The controller circuit is still further configured to control one or more fluid control devices, responsive to said identifying.

It is to be understood that both the foregoing general description and the following detailed description are exemplary and explanatory in nature, and are intended to provide an understanding of the presently disclosed techniques and apparatus without limiting the scope of those techniques and apparatus. In that regard, additional aspects, features, and advantages of the presently disclosed techniques and apparatus will be apparent to those skilled in the art from the following detailed description and the accompanying figures.

DETAILED DESCRIPTION

Figure 1:
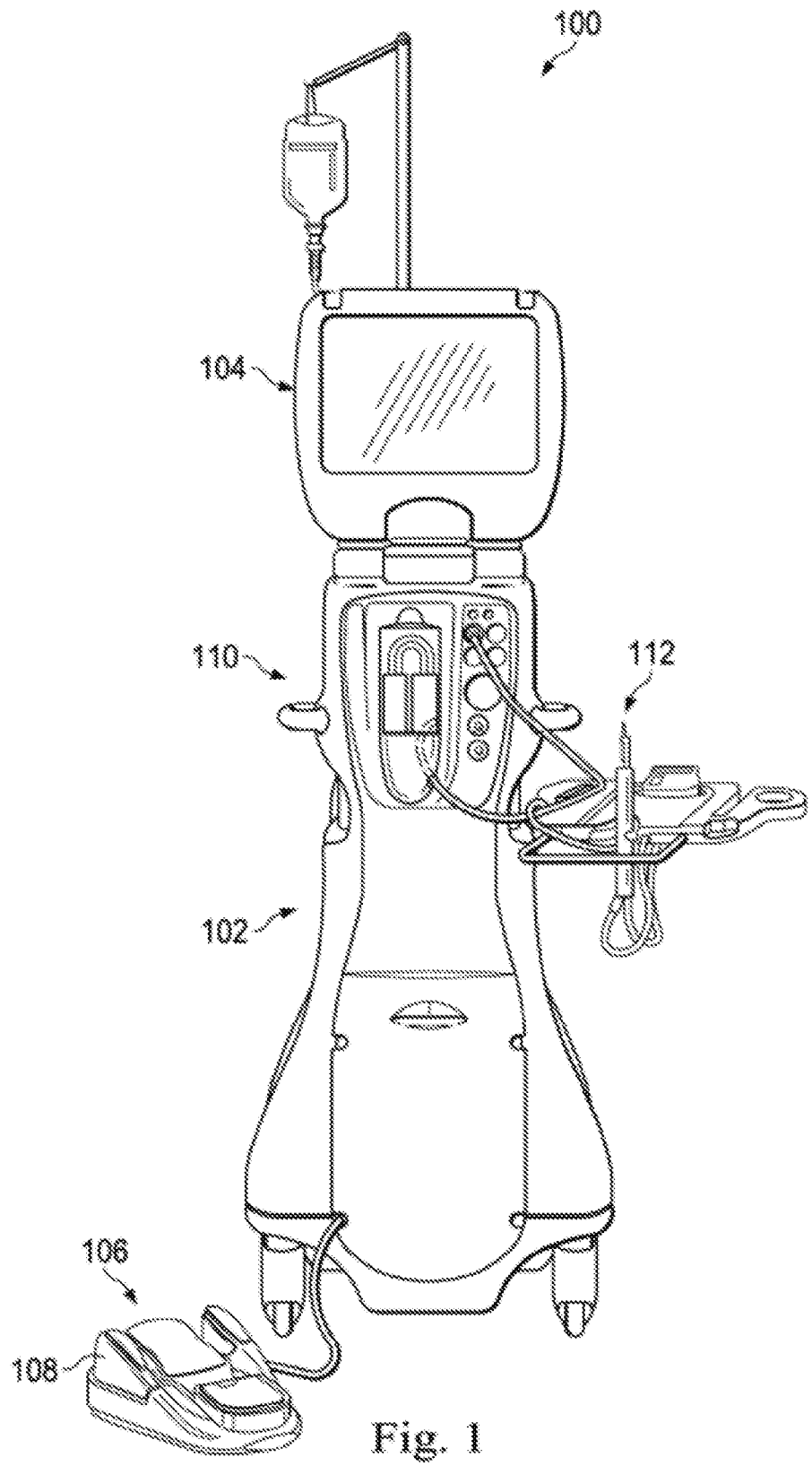
FIG. 1 shows an example phacoemulsification surgical console.

For the purposes of promoting an understanding of the principles of the present disclosure, reference will now be made to the example embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for fluidics system control. More particularly, the disclosure relates to the use of frequency-domain signal processing of pressure sensor signals and/or flow signals, to provide on-demand control of multi-component fluidic systems such as phacoemulsification systems.

Figure 2:
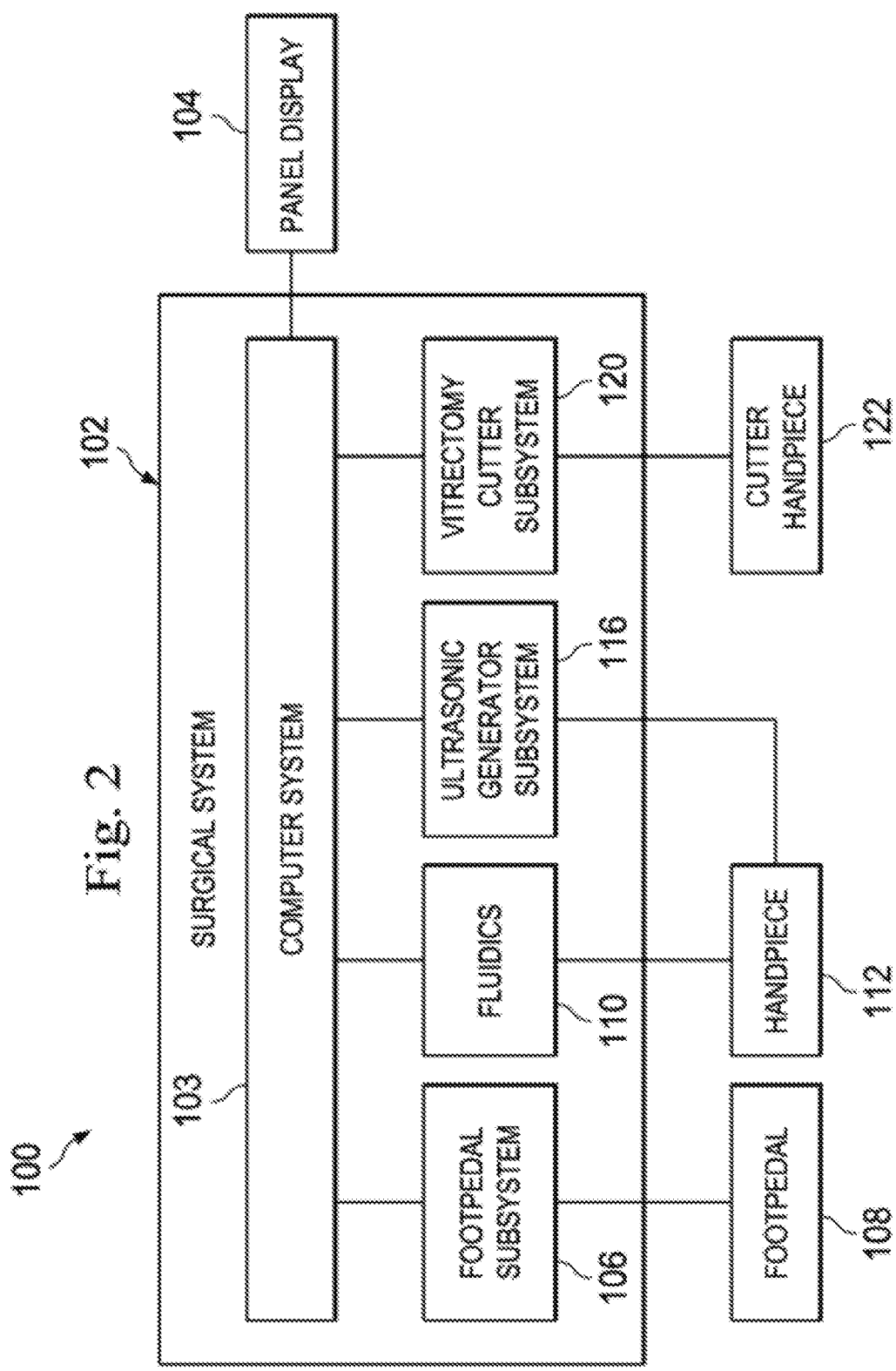
FIG. 2 is a block diagram of the phacoemulsification console of FIG. 1 showing various subsystems thereof.

FIG. 1 illustrates an exemplary phacoemulsification surgical console, generally designated 100. FIG. 2 is a block diagram of the console 100 showing various subsystems that operate to perform a phacoemulsification procedure. The console 100 includes a base housing 102 with a computer unit 103 and an associated display screen 104. In some implementations, the display screen 4 is adapted to show data relating to operation and performance of the console 100 during a phacoemulsification surgical procedure. The console 100 also includes a number of subsystems that may be used together to perform a phacoemulsification surgical procedure. For example, the subsystems may include one or more of a foot pedal subsystem 106 including, for example, a foot pedal 108, a fluidics subsystem 110 including a hand-held surgical instrument shown as hand piece 112, an ultrasonic generator subsystem 116 that is operable to cause a needle of the hand piece 112 to oscillate ultrasonically, and a pneumatic vitrectomy cutter subsystem 120 including a vitrectomy hand piece 122. These subsystems may overlap and cooperate to perform various aspects of a procedure or may be operable separately and/or independently from each other during one or more procedures. That is, some procedures may utilize one or more subsystems while excluding others.

Figure 3:
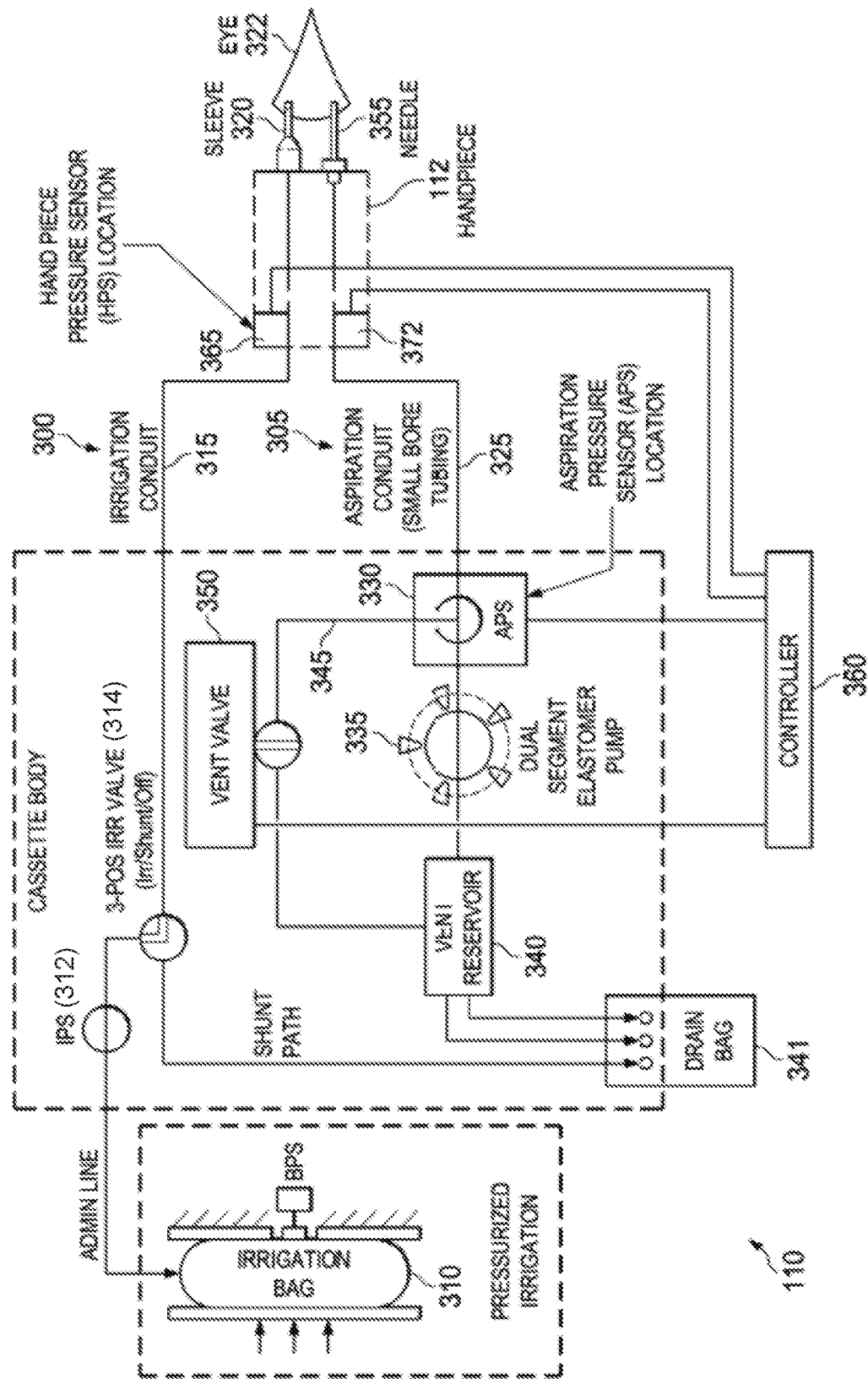
FIG. 3 is a schematic of an example fluidics subsystem that may be usable with the phacoemulsification surgical console of FIGS. 1 and 2.

FIG. 3 illustrates a schematic showing the fluidics subsystem 110 and the hand piece 112. The fluidics subsystem 110 includes an irrigation system 300 and an aspiration system 305 in fluid communication with the hand piece 112.

In some implementations, the irrigation system 300 includes an irrigation fluid source 310 and a flexible irrigation conduit 315 in fluid communication with a sleeve 320 located on the hand piece 112. The irrigation system 300 extends between the irrigation fluid source 310 and the hand piece 112, and carries fluid to the surgical site. For example, in FIG. 3, the surgical site is identified as an eye 322. In some implementations, the sterile fluid is a saline fluid; however, other fluids may be used.

In some instances, the irrigation fluid source 310 may be a mechanically pressurized fluid source. For example, in some implementations, the irrigation fluid source 310 may include a clamping pressure system as shown in FIG. 3. A clamping pressure system may include a fluid source contained in a flexible container disposed between rigid elements. The rigid element may be moveable relative to each other, and the rigid elements are operable to apply a selectable compressive force to the flexible container to produce a desired fluid pressure within the flexible container. A pressure sensor (BPS) may also be included. The BPS may sense a pressure associated with the irrigation fluid source 310. For example, in an implementation where the irrigation fluid source 310 is a flexible bag filled with irrigation fluid compressed by a rigid moveable element, the BPS may detect a pressure exerted by the bag. The sensed pressure from the BPS may be used to control a force applied to the irrigation fluid source 310 by the camping pressure system.

The irrigation system 300 may also include an irrigation fluid pressure sensor (IPS) 312 disposed between the irrigation fluid source 310 and the hand piece 112. The irrigation fluid pressure sensor 312 is operable to sense a pressure of the irrigation fluid. A three-position valve 314 may also be included in the irrigation system 300. The three-position valve 314 is selectively moveable to provide fluid communication between a line extending from the irrigation fluid source 310 and a line extending to the hand piece 112. The valve 314 may be selectively positioned to provide communication between the irrigation fluid source 310 and a waste reservoir or drain bag 341, described in more detail below. Thus, irrigation may be selectively provided from the irrigation fluid source 310 and the hand piece 112 or from the irrigation fluid source 310 to the waste reservoir 341. A position of the valve 314 may be selected by a user.

In other implementations, the irrigation fluid source 310 may include a gravity-fed fluid system. For example, in some instances, the irrigation fluid source 310 may include a fluid source suspended by an intravenous (IV) pole. Adjusting the elevation of the fluid source is operable to control the pressure head of the fluid within the fluid source and, consequently, a flow rate of the fluid through the irrigation conduit 315 to the surgical site. Other fluid sources also are contemplated.

The aspiration system 305 includes an aspiration conduit 325 located in fluid communication with the hand piece 112, an aspiration pressure sensor 330, a pump 335 interfacing with the aspiration conduit 325, and a vent reservoir 340. In some implementations, the pump 335 may be a dual segment elastomer pump operable to pump peristaltically. In other implementations, the pump 335 may be a single segment elastomer pump. In still other implementations, the pump 335 may have any number of elastomeric segments. In other instances, the pump 335 may be any suitable pump operable to pump fluid. In some implementations, the vent reservoir 340 may be a drain bag or an intersection of conduits. Other vent reservoirs also are contemplated. As can be seen, the aspiration system 305 extends from the surgical site (i.e., the eye 322 for the implementation illustrated in FIG. 3) to the vent reservoir 340 and ultimately on to the drainage or waste reservoir 341.

The pump 335 is operable to create a vacuum pressure within the aspiration conduit 325 between the pump 335 and the eye 322 to draw the aspiration fluid from the surgical site and into the vent reservoir 340. A bypass conduit 345 is also in fluid communication with the aspiration conduit 325 and the vent reservoir 340 and bypasses the pump 335. A vent valve 350 is located along the bypass conduit 345 and is operable to control the vacuum pressure within the aspiration conduit 325 by opening and closing, thereby respectively opening bypass conduit 345 to the atmosphere and isolating the bypass conduit 345 from the atmosphere.

Figure 4:
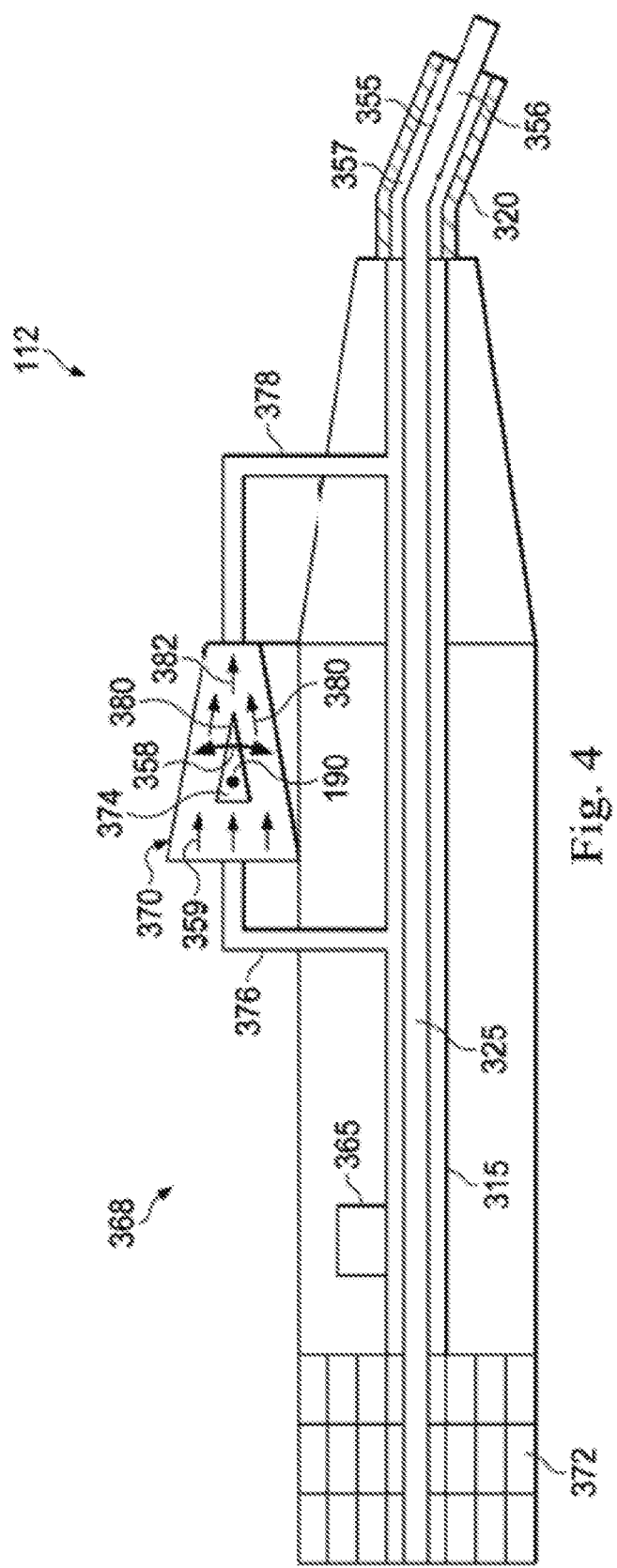
FIG. 4 is a schematic of an example hand piece that may be usable with the phacoemulsification surgical console of FIGS. 1 and 2.

The example hand piece 112 is shown schematically in FIG. 3, and is shown in greater detail in FIG. 4. In the example illustrated, the hand piece 112 includes a portion of the irrigation system 300 (e.g., a portion of irrigation conduit 315) and a portion of the aspiration system 305 (e.g., a portion of aspiration conduit 325). For explanatory purposes only, FIG. 3 shows the sleeve 320 and the needle 355 adjacent each other. In use, however, the sleeve 320 and needle 355 are coaxial for insertion into the surgical site. That is, in some implementations, the needle 355 extends through the sleeve 320 in a coaxial arrangement.

FIG. 4 shows the example hand piece 112 in greater detail. Referring to FIG. 4, the hand piece 112 includes a portion of the irrigation conduit 315 and a portion of the aspiration conduit 325. The needle 355 extends through the sleeve 320 to define an annular space 357. The irrigation conduit 315 communicates with the annular space 357. The aspiration conduit 325 communicates with the needle 355. Irrigation fluid flows through the irrigation conduit 315, and through the annular space 357. Ultimately, the irrigation fluid is conducted to a surgical site, such as the eye 322 shown in FIG. 3. The aspiration conduit 325 transports fluid and emulsified particles from the lumen 356 of the needle 355 to the aspiration system 305 during the surgical procedure.

In the illustrated example, the hand piece 112 also includes a pressure sensor 365 and an acoustic streaming arrangement 368. The pressure sensor 365 is disposed in the hand piece 112 along the irrigation conduit 315. Although shown at the proximal end of the hand piece 112, in other embodiments, the pressure sensor 365 may be disposed at the distal end. In some instances, the pressure sensor 365 may be disposed proximate the sleeve 320. However, the pressure sensor 365 may be positioned at any location along the hand piece 112.

In some implementations, the pressure sensor 365 is an irrigation pressure sensor 365 located along the irrigation conduit 315 within the hand piece 112. The irrigation pressure sensor 365 is operable to detect an irrigation pressure within the irrigation conduit 315. In other implementations, the pressure sensor 365 is in fluid communication with the surgical site through a communication element. In some implementations, the communication element is an element other than the irrigation conduit 315. For example, the pressure sensor 365 may be disposed within its own separate tube or probe that is in communication with the surgical site. For example, in some instances, the separate tube or probe may be independent of the hand piece 112 but permits the pressure sensor 365 to be disposed within close proximity of the surgical site. In alternative embodiments, the pressure sensor 365 may be disposed within or on the sleeve 320 or elsewhere on the hand piece 112.

In the example system shown in FIG. 3, the acoustic streaming arrangement 368 includes an acoustic chamber 370 and a vibration-generating driving device 372. The acoustic chamber 370 is a fluid-filled chamber that includes a flow generator 374 and is disposed in communication with the irrigation conduit 315 via first and second shunt lines 376 and 378. In the example handset shown in FIG. 4, the first shunt line 376 extends from the irrigation conduit 315 at a proximal location thereof, and a second shunt line 378 extends from the irrigation conduit 315 at a distal location thereof. As will be explained below, in the event of a detected post-occlusion surge, the flow generator 374 generates fluid flow through the first and second shunt lines 376 and 378 to mitigate a drop in IOP. In some embodiments, the shunt line 376 connects the acoustic chamber 370 to a fluid reservoir separate from the irrigation conduit 315.

When activated, the flow generator 374 is configured to draw fluid through the first shunt line 376 and output fluid flow through the second shunt line 378. This fluid flow through the second shunt line 378 is introduced into the irrigation conduit 315, thereby increasing an overall fluid flow that is ultimately introduced into a surgical site, such as the eye 322 shown in FIG. 3. In some implementations, the flow generator 374 is a wedge-shaped blade. In some implementations, the flow generator 374 is a microscopic wedge-shaped blade. The flow generator 374 is arranged in the acoustic chamber 370 and is operable to vibrate back and forth about a pivot 190 in the direction of the arrow 358, as indicated in FIG. 4. In other implementations, the flow generator may be operable to laterally oscillate in a side-to-side motion.

Returning to FIG. 3, the fluidics subsystem 110 also includes a controller 360. The controller 360 is operable to communicate with the pressure sensor 365 located within the hand piece 112, the aspiration pressure sensor 330, the vent valve 350, and the driving device 372, and may be further operable to communicate with one or more other pressure sensors, fluid flow sensors, and/or control devices, such as valves or pressure regulation devices. The controller 360 may include a processor and memory that may include an executable program for operating the features of the fluidics subsystem. Thus, the controller 360 may be operable to control operation of the driving device 372 and/or other fluid control mechanisms, as well as to receive signals from the sensors 365 and 330 and/or one or more other pressure sensors and/or fluid flow sensors. In some instances, the sensor 330 may be located in a surgical console and may be configured to measure aspiration pressure. Consequently, data sensed by the sensor 330 may be utilized to control an aspiration vacuum level. In some instances, the controller 360 is a PID controller configured to control the driving device 372 or other control mechanisms to mitigate pressure deviations, such as those that occur during post-occlusion surge. For example, the controller 360 may be operable to receive the signals from sensor 365 and/or sensor 330 and determine whether a post-occlusion surge has occurred. In the particular example illustrated in FIGS. 3 and 4, if a post occlusion surge is detected, the controller is operable to cause the acoustic streaming device to increase the flow rate of fluid provided to the eye 322.

In some implementations, the controller 360 may include one or more pre-established pressure thresholds establishing desired pressure limits. When a measured or detected pressure passes beyond these pre-established pressure thresholds, the controller 360 controls the driving device 372 and/or other one or more other control mechanisms to restore the pressure to a desired level. In some implementations, the pressure thresholds may be a function of intraocular pressure (IOP). The controller 360 may include a pressure threshold relating to the irrigation pressure as a representation of IOP. This may be, for example, a pressure threshold set below pressures at which the system operates under normal conditions (without occlusions or occlusion breaks). These pressure thresholds may be input by an operator or may be preset and stored during manufacturing or at any other time.

As explained above, the controller 360 may also receive information from the irrigation pressure sensor 365 and aspiration pressure sensor 330. The controller 360 may thus be further configured to control the operation of the driving device 372 or other devices based on the information received from the irrigation pressure sensor 365 and the aspiration pressure sensor 330. As indicated above, the pressure sensor 365 may be located on the hand piece 112 close to the surgical site. In some instances, the pressure sensor 365 may be disposed less than 12 inches from the surgical site. From its location in the hand piece 112, the irrigation pressure sensor 365 detects a fluid pressure representative of with the surgical site. The proximity to the eye 322 of sensor 365 enables quick detection of changes in pressure (e.g., as may occur during an occlusion break) and allows for a rapid response to a detected post-occlusion surge. For example, the rapid response may significantly diminish or eliminate post-occlusion surges. For example, in some instances, pressure changes may be detected as quickly as within 50 milliseconds of an occlusion break. Such a fast response time may enable the controller 360 to quickly provide a response to pressure deviations before IOP is negatively affected.

In operation, irrigation fluid is provided to a surgical site (e.g., eye 322 shown in FIG. 3) through the irrigation conduit 315. In the example shown in FIG. 4, the irrigation pressure sensor 365 is located along the irrigation conduit 315 to detect the pressure of the irrigation fluid within the irrigation conduit 315. The controller 360 continuously monitors the pressure of the irrigation fluid using the irrigation pressure sensor 365. For example, if the pressure of the irrigation fluid drops below the selected pressure threshold, as may occur during a post-occlusion surge, the controller 360 may activate the driving device 372, which in turn vibrates the flow generator 374 in the acoustic chamber 370. Because the acoustic chamber 370 is filled with fluid from the irrigation conduit 315 via, the first shunt line 376, activation of the flow generator 374 initiates an acoustic stream of fluid into the second shunt line 378 which results in a shot or burst of additional irrigation fluid being introduced to the eye 322. This shot of fluid may reduce or eliminate the drop in IOP that results from an occlusion break or post-occlusion surge. The acoustic chamber 370 is continuously filled with irrigation fluid from the irrigation conduit 315 via the first shunt line 376. Hence a fluid level within the acoustics chamber 370 is maintained.

In some implementations, the driving device 372 may continue to vibrate the flow generator 374 until the pressure, indicates the IOP 322 in the eye is stabilized. The irrigation pressure sensor 365 or the aspiration pressure sensor 330 may be used to detect whether IOP in the eye 322 has stabilized. The controller 360 may determine whether the IOP has stabilized by comparing signals received from the irrigation pressure sensor 365 and/or the aspiration pressure sensor corresponding to fluid pressure to a selected pressure threshold. As indicated above, there may be more than one pressure threshold. Also, one or more of the pressure thresholds may be entered by a user or stored in the controller 360 at the time of manufacturing.

In some implementations, the controller 360 may be operable to stop the driving device 372 without receipt of a measurement from the irrigation sensor 365 and/or the aspiration sensor 330. For example, in some instances, the driving device 372 may operate to provide supplementary irrigation fluid into the eye 322 for a selected period of time. The driving device 372 and, hence the flow generator 374, would be deactivated after a selected period of time. Thus, an increased flow rate of irrigation may be provided to the eye 322 or any other surgical site for a selected period of time and then discontinued. Accordingly, in such implementations, the controller 360 is operable to stop the driving device 372 after a preset period of time rather than for a period of time based on a detected pressure measurement.

As briefly discussed above, control of the fluid flow in a system like that pictured in FIGS. 3 and 4 is complicated by the fact that events such as post-occlusion surge and water hammer may, in some cases, have effects on fluid pressures in the system that are on the same order of magnitude as changes in pressure caused by the equipment user's interaction with the equipment, or on the same order of magnitude as noise in the feedback signals. This can make it difficult for the controller 360 to discern the difference between those signals for which immediate compensation by the control system is desirable, and those signals for which rapid compensation is less desirable.

These events can be easily differentiated from one another and from noise in the frequency-domain, as long as the either the frequency content or the phase(s) of the signals are distinguishable, which usually is the case. Hence, if controller 360 includes a processor that is fast enough to process the signals to calculate the frequencies and phases of one or more of the monitored pressure and/or flow signals, e.g., by converting the monitored signals to the frequency-domain using Fast Fourier Transforms (FFTs), an on-demand control system based on sensing the differences in the frequencies and/or phase can be deployed.

In some embodiments of this approach, the natural frequencies and phase relationships of the signals in a system are evaluated, to establish a baseline understanding of what frequency characteristics and phase relationships are expected for normal operation of the system. This may include, for example, an evaluation and characterization of the frequency characteristics of noise in the monitored signals, as well as a characterization of the frequency characteristics and phase changes corresponding to movement of equipment components. Likewise, various events, such as post-occlusion surge and water hammer can be triggered and/or simulated, to evaluate the frequency characteristics and/or phase changes that are characteristic to these events. This evaluation is then used to provide controller 360 with one or more thresholds, limits, windowing functions, correlations, etc., to be applied to the frequency-domain versions of the monitored signals. These parameters can be used to map any deviations in the signals' frequency and/or phase characteristics to a particular adverse event, for example, and in turn to allow the controller 360 to respond appropriately by controlling the appropriate control devices.

One example where this approach may be employed is for occlusion surge mitigation for active fluidics in the system illustrated in FIGS. 3 and 4. Conventionally, a raw (time-domain) signal from the hand-piece pressure sensor may be used to detect the occlusion break, where the controller 360 then mitigates the surge by activating a variable vent valve and/or controlling the driver device 372 as described in detail above. However, using time-domain processing, it could be difficult in some scenarios to distinguish signals resulting from an occlusion break from signal changes that are occurring due to a change in sleeve resistance to the fluid flow, as might arise from normal twisting of the sleeve during the surgery. The pressure signals resulting from these signals can be easily distinguished from one another in the frequency-domain, since the changes in frequency content of the signal are typically much more significant in the event of an occlusion break, compared to those arising from an increase in flow resistance. By distinguishing between these and other events, controller 360 can respond appropriately to mitigate post-occlusion surges, while refraining from changes to the control system for less detrimental events.

Another example where frequency-domain processing is useful is in flow compensation. Active fluidics control in equipment like that pictured in FIGS. 3 and 4 (as well as in other fluid control systems more generally) works well if flow resistance changes can be detected and/or predicted accurately. Generally, changes in the flow resistance are monitored with the help of two accurate pressure sensors. However, estimating the flow resistance may be impaired if changes in fluid flow occur due to other real disturbances, rather than from flow resistance in the system. Frequency-domain processing of the pressure monitoring signals can be used to evaluate the changes in frequency and/or phases of the signals, to get an indication of when the flow resistance changes, as distinguished from other events with different frequency/phase characteristics. All the lines used in the fluid distribution system can be characterized as real transmission lines, with corresponding compliances. Therefore, when the flow resistance changes, it will also change the compliance of the corresponding fluid line/transmission line, which will in turn change the frequency/phase response of the system. These changes can be discerned and distinguished from other disturbances, thus allowing a controller to more accurately compensate for flow resistance changes in the fluidic system.

Figure 5:
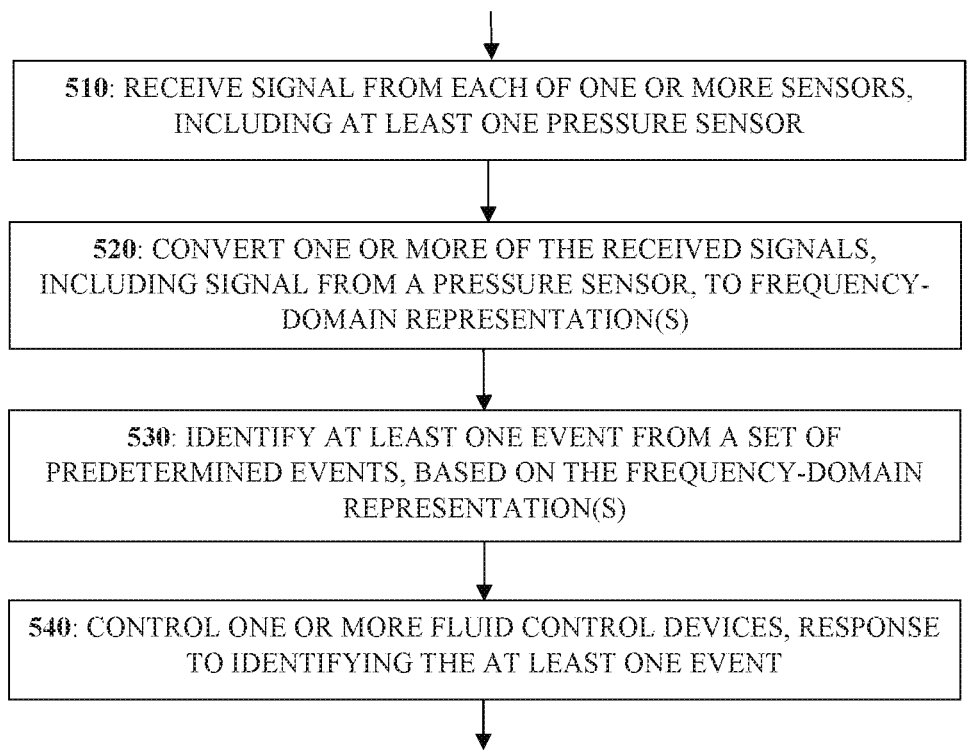
FIG. 5 is a flow chart of an example method in a phacoemulsification system.

FIG. 5 illustrates an example method for fluid control in a phacoemulsification, according to several embodiments of the techniques described above. As shown at block 510, the method includes receiving a signal from each of one or more sensors, including at least one pressure sensor. As shown at block 520, the method includes converting each of one or more of the received signals, including a signal from a pressure sensor, to a corresponding frequency-domain representation of the received signal.

The method further includes, as shown at block 530, identifying at least one event from a set of predetermined events, based on the frequency-domain representations of received signals. Finally, as shown at block 540, the method includes controlling one or more fluid control devices, responsive to identifying the at least one event.

The frequency-domain representations of the received signals may each be generated using a Fast Fourier Transform (FFT), for example, although other frequency-domain representations and/or conversion algorithms may be used. A frequency-domain representation generated with a FFT typically includes at least a magnitude value for each of a plurality of frequency components, or "bins"; the frequency-domain representation may include phase information in some embodiments, e.g., as embedded in complex values for each frequency component. Accordingly, some embodiments of the illustrated embodiments may evaluate only scalar magnitudes from the frequency-domain representation, while others may evaluate phase information as well, either separately from scalar magnitudes, or implicitly, as part of evaluating complex values for the frequency components of the frequency-domain representation. Thus, identifying the at least one event may be based on frequency magnitude information, phase information, or both.

The conversion of sensor signals to the frequency domain, as described above, is typically repeated, e.g., periodically, to produce a time series of frequency-domain representations for evaluation. Thus, in some embodiments, identifying the at least one event is based, at least in part, on detecting that a change, over time, in the frequency-domain representation of at least one of the received signals meets one or more predetermined criteria. These criteria may be based on predetermined thresholds, ratios, windows, and the like. In some of these and in some other embodiments, identifying the at least one event may be based, at least in part, on detecting that a difference between a predetermined baseline pattern and the frequency-domain representation of at least one of the received signals meets one or more predetermined criteria. As discussed above, the predetermined baseline pattern may be obtained from measurements and/or simulations of the subject system.

In the example method illustrated in FIG. 5, a frequency-domain representation of at least one signal from a pressure signal is used. This may be, for example, a pressure sensor disposed in a phacoemulsification hand-piece and configured to monitor a pressure in an irrigation conduit of the phacoemulsification hand-piece. In this particular example, the step of converting each of one or more of the received signals to a frequency-domain representation includes converting the signal from the pressure sensor disposed in the phacoemulsification hand-piece to a corresponding frequency-domain representation. Likewise, the identifying of the at least one event is based on the frequency-domain representation of the signal from the pressure sensor disposed in the phacoemulsification hand-piece. The identified event may be a post-occlusion surge event, for example.

In some embodiments, the one or more sensors may also include a fluid flow sensor, where the converting of each of one or more of the received signals to a frequency-domain representation includes converting the signal from the fluid flow sensor to a corresponding frequency-domain representation, and the identifying of the at least one event is based on the frequency-domain representation of the signal from the fluid flow sensor, as well as the frequency-domain representation of at least one pressure sensor signal.

In some embodiments, the one or more sensors may include two pressure sensors disposed at two points along an irrigation path in the phacoemulsification system, where the signals from each of these two pressure sensors are converted to corresponding frequency-domain representations, with the resulting frequency-domain representations used to identify the at least one event is based on the frequency-domain representations of the signals from the two pressure sensors. The identified event may be, for example, a change in flow resistance of the irrigation path; in some embodiments, the frequency-domain representations may be used to estimate a degree of change in flow resistance, where the degree of change may dictate whether, and/or to what extent, a compensating control response is generated.

In any of the embodiments discussed above, the controlling of the one or more fluid control devices may include one or more of the following for example: opening or closing a fluid valve in an irrigation path; opening or closing a valve in an aspiration path; controlling a pressurizing device to decrease or increase a pressure in an irrigation path; and controlling a pressurizing device to decrease or increase a pressure in an aspiration path.

Figure 6:
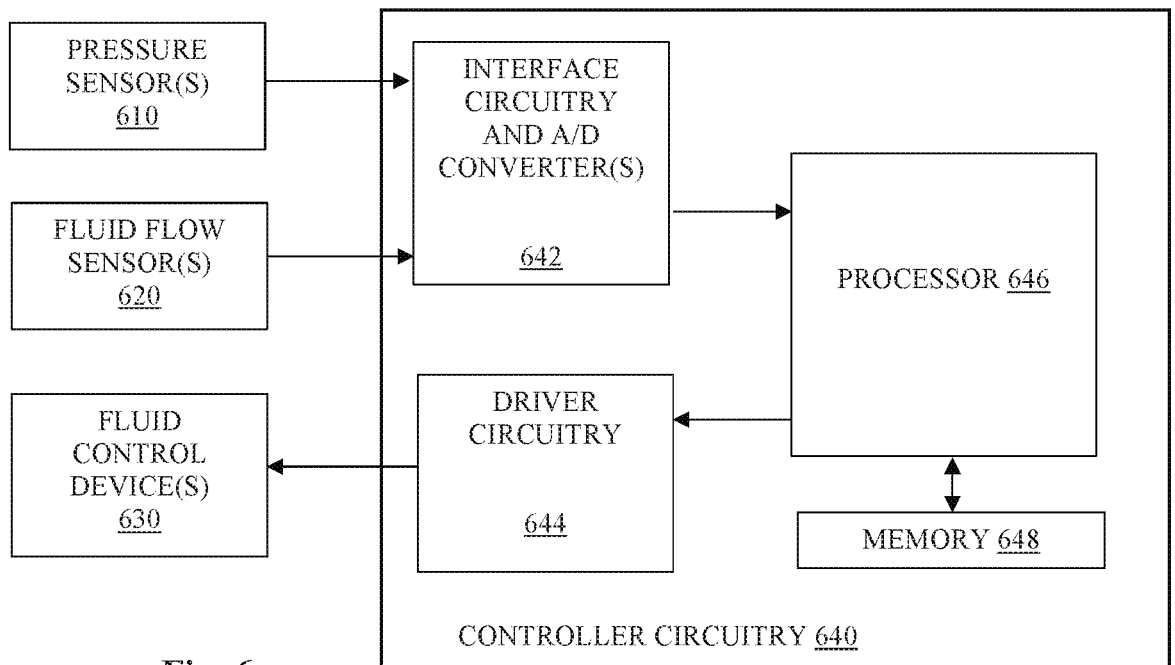
FIG. 6 is a schematic of an example control system.

FIG. 6 illustrates an example control system for a phacoemulsification system, where the control system includes one or more sensors. As seen in the figure, the one or more sensors include at least one pressure sensor 610, and may further include one or more fluid flow sensors 620. The example control system further includes one or more fluid control devices 630, as well as controller circuitry 640, which is operatively coupled to the one or more sensors 610 and 620 and the one or more fluid control devices 630.

Controller circuitry 640 is configured to receive a signal from each of one or more pressure sensors 610 and, if present, the one or more fluid flow sensors 620. As seen in the figure, controller circuitry 640 may include interface circuitry and one or more analog-to-digital (ND) converters 642, to convert analog signals from the sensors into a digital format. In some embodiments, one or more of the sensors may include A/D converters, or otherwise produce a sensor signal with a digital format, in which case controller circuitry 640 need not convert that sensor signal to digital.

Controller circuitry 640 is further configured to convert each of one or more of the received signals, including at least a signal from a pressure sensor 610, to a frequency-domain representation of the received signal. In the illustrated example, this conversion is performed by processor 646, which may be programmed, e.g., with program instructions stored in memory 648, to carry out an FFT on each of one or more of the digital sensor signals. Again, however, it will be appreciated that frequency-domain representations produced by transforms other than the Fourier Transform may be used (e.g., Laplace transforms or Z-transforms), and algorithms other than the well-known FFT algorithm may be used. Furthermore, while the transformation of the sensor signal(s) into the frequency domain is performed by processor 646 in the illustrated example system, other embodiments may use dedicated digital logic to carry out all or part of the conversion of sensor signals into the frequency domain. Finally, it should be appreciated that this conversion is typically repeated, e.g., periodically, to produce a time series of frequency-domain representations for evaluation.

Controller circuitry 640 is still further configured to identify, based on the frequency-domain representations of received signals, at least one event from a set of predetermined events. In the example system shown in FIG. 6, this identification operation is carried out by processor 646, e.g., using predetermined threshold, parameters, baseline patterns, etc., stored in memory 648, where the predetermined events are defined by the satisfaction of certain criteria involving these stored thresholds, parameters, baseline patterns, etc.

Finally, controller circuitry 640 is configured to control one or more of the fluid control devices 630, responsive to identifying a predetermined event. In the illustrated example, this is carried out by processor 646, which controls driver circuitry 644 to control the one or more fluid control devices 630. The particulars of the control signals and/or interface circuitry needed with any given fluid control device are well known to designers of phacoemulsification systems and other multi-component fluidic control systems.

As discussed above in connection with FIG. 5, in some embodiments at least one of the frequency-domain representations comprises phase information. In these embodiments, the controller circuitry 646 may be configured to identify the at least one event based on the phase information. In some embodiments, controller circuitry 646 is configured to identify the at least one event based on detecting that a change, over time, in the frequency-domain representation of at least one of the received signals meets one or more predetermined criteria. In some of these and in some other embodiments, controller circuitry 646 is configured to identify the at least one event based on detecting that a difference between a predetermined baseline pattern and the frequency-domain representation of at least one of the received signals meets one or more predetermined criteria.

In the system illustrated in FIG. 6, a frequency-domain representation of at least one signal from a pressure signal is used. This may be, for example, a pressure sensor disposed in a phacoemulsification hand-piece and configured to monitor a pressure in an irrigation conduit of the phacoemulsification hand-piece. In this particular example, the controller circuitry 646 converts the signal from the pressure sensor disposed in the phacoemulsification hand-piece to a corresponding frequency-domain representation, and identifies the at least one event based (at least in part) on the frequency-domain representation of the signal from the pressure sensor disposed in the phacoemulsification hand-piece. The identified event may be an occlusion break or post-occlusion surge event, for example.

In some embodiments, at least one fluid flow sensor 620 is present, where controller circuitry 646 is configured to convert the signal from the fluid flow sensor to a corresponding frequency-domain representation. In some of these embodiments, controller circuitry 646 is configured to identify the at least one event based (at least in part) on the frequency-domain representation of the signal from the fluid flow sensor 620.

In some embodiments, the one or more sensors 610 may include two pressure sensors disposed at two points along an irrigation path in the phacoemulsification system, where the signals from each of these two pressure sensors are converted by controller circuitry 646 to corresponding frequency-domain representations, with the resulting frequency-domain representations used by controller circuitry 646 to identify the at least one event is based on the frequency-domain representations of the signals from the two pressure sensors. The identified event may be, for example, a change in flow resistance of the irrigation path; in some embodiments, the frequency-domain representations may be used to estimate a degree of change in flow resistance, where the degree of change may dictate whether, and/or to what extent, a compensating control response is generated.

In various embodiments, controller circuitry 646 is configured to control at least one of the following, responsive to identifying the at least one event: a fluid valve in an irrigation path; a valve in an aspiration path; a pressurizing device configured to selectively decrease or increase a pressure in an irrigation path; and a pressurizing device configured to selectively decrease or increase a pressure in an aspiration path. Several examples of these and other control devices are shown in FIGS. 3 and 4; designers of phacoemulsification systems will be aware of other fluid control devices that may be applicable to these systems and controllable using the techniques described herein.

It should be noted that while FIGS. 3 and 4 illustrate details of an example phacoemulsification system, and in particular describe details of a phacoemulsification hand piece that includes an acoustic streaming arrangement, the methods illustrated in FIG. 5 and the control system illustrated in FIG. 6, and variants thereof, are more generally application to fluid control in any of a wide variety of phacoemulsification systems, including those using irrigation and/or aspiration subsystems different from those illustrated in FIGS. 3 and 4. More generally, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A control system for a phacoemulsification system, the control system comprising:
   one or more sensors, the one or more sensors comprising at least one pressure sensor;
   one or more fluid control devices; and
   controller circuitry operatively coupled to the one or more sensors and the one or more fluid control devices and programmed to:
      receive a time-domain signal from each of the one or more sensors, the time-domain signal having a magnitude, wherein the magnitude of the time-domain signal when detecting a surgical event is similar to a magnitude of the time-domain signal caused by a user's interaction with the phacoemulsification system or noise in the time-domain signal;
      convert each of the one or more of the received time-domain signals to a frequency-domain representation of the received time-domain signal, said one or more of the received time-domain signals comprising at least one time-domain signal from a pressure sensor, said frequency domain representation comprising frequency and/or phase information of the received time-domain signal, wherein the frequency and/or phase information distinguishes the surgical event from the user's interaction with the phacoemulsification system or from noise in the system;
      identify, based on the frequency-domain representations of received time-domain signals, at least one event from a set of predetermined events by evaluating the frequency and/or phase information of the frequency representation of the received time-domain signal; and
      control one or more fluid control devices, responsive to said identifying.

2. The control system of claim 1, wherein the controller circuitry is programmed to identify the at least one event based on detecting that a change, over time, in the frequency-domain representation of at least one of the received time-domain signals meets one or more predetermined criteria.

3. The control system of claim 1, wherein the controller circuitry is programmed to identify the at least one event based on detecting that a difference between a predetermined baseline pattern and the frequency-domain representation of at least one of the received time-domain signals meets one or more predetermined criteria.

4. The control system of claim 1, wherein:
   the one or more sensors comprise a fluid flow sensor; and
   the controller circuitry is programmed to convert the time-domain signal from the fluid flow sensor to a corresponding frequency-domain representation and to identify the at least one event based on the frequency-domain representation of the time-domain signal from the fluid flow sensor.

5. The control system of claim 1, wherein:
   the one or more sensors comprise a pressure sensor disposed in a phacoemulsification hand-piece and configured to monitor a pressure in an irrigation or aspiration conduit of the phacoemulsification hand-piece; and
   the controller circuitry is programmed to convert the time-domain signal from the pressure sensor disposed in the phacoemulsification hand-piece to a corresponding frequency-domain representation and to identify the at least one event based on the frequency-domain representation of the time-domain signal from the pressure sensor disposed in the phacoemulsification hand-piece.

6. The control system of claim 5, where the controller circuitry is programmed to identify a post-occlusion surge event, based on the frequency-domain representation of the time-domain signal from the pressure sensor disposed in the phacoemulsification hand-piece.

7. The control system of claim 1, wherein:
   the one or more sensors comprise two pressure sensors disposed at two points along an irrigation path in the phacoemulsification system;
   the controller circuitry is programmed to convert the time-domain signals from each of the two pressure sensors to corresponding frequency-domain representations and to identify the at least one event based on the frequency-domain representations of the time-domain signals from the two pressure sensors.

8. The control system of claim 7, wherein the controller circuitry is programmed to identify a change in flow resistance of the irrigation path based on the frequency-domain representations of the time-domain signals from the two pressure sensors.

9. The control system of claim 1, wherein the controller circuitry is programmed to control at least one of the following, responsive to identifying the at least one event:
   a fluid valve in an irrigation path;
   a valve in an aspiration path;
   a pressurizing device configured to selectively decrease or increase a pressure in an irrigation path; and
   a pressurizing device configured to selectively decrease or increase a pressure in an aspiration path.

10. The control system of claim 1 wherein the controller circuitry is programmed to identify a post-occlusion surge event based on the frequency-domain representation of the time-domain signal.

11. The control system of claim 1 wherein the controller circuitry is programmed to identify a fluid flow change, based on the frequency-domain representation of the time-domain signal.

12. The control system of claim 1 wherein the controller circuitry is programmed to evaluate and characterize frequency and/or phase characteristics of noise in the time-domain signal and frequency and/or phase changes corresponding to movement of equipment components.

13. The control system of claim 1 wherein the controller circuitry is programmed to evaluate and characterize frequency and/or phase characteristics of a post-occlusion surge event and control the one or more fluid control devices based on the frequency and/or phase characteristics of the post-occlusion surge event.

14. The control system of claim 1 wherein the controller circuitry is programmed to distinguish between a frequency domain representation of the time-domain signal resulting from an occlusion break event and a frequency domain representation of the time-domain signal resulting from a change in fluid flow due to sleeve resistance, wherein a change in a frequency content of the frequency domain representation of the time-domain signal is more significant during the occlusion break event than during the change in fluid flow due to sleeve resistance.

15. The control system of claim 1 wherein the controller circuitry is programmed to monitor a frequency domain representation of the time-domain signal of flow resistance in the system and to detect a change in the flow resistance in the system by detecting a change in the frequency and/or phase response of the system caused by a change in compliance of a fluid line.

* * * * *